United States Patent
O'Meara et al.

(10) Patent No.: US 8,460,945 B2
(45) Date of Patent: Jun. 11, 2013

(54) METHOD FOR MONITORING STATUS OF SYSTEM COMPONENTS

(75) Inventors: David L. O'Meara, Poughkeepsie, NY (US); Daniel Craig Burdett, West Park, NY (US); Stephen H. Cabral, Pine Plains, NY (US); Gert Leusink, Saltpoint, NY (US); John William Kostenko, LaGrangeville, NY (US); Cory Wajda, Hopewell Junction, NY (US)

(73) Assignee: Tokyo Electron Limited, Tokyo (JP)

( * ) Notice: Subject to any disclaimer, the term of this patent is extended or adjusted under 35 U.S.C. 154(b) by 2102 days.

(21) Appl. No.: 10/673,513

(22) Filed: Sep. 30, 2003

(65) Prior Publication Data

US 2005/0068519 A1    Mar. 31, 2005

(51) Int. Cl.
*H01L 21/00* (2006.01)

(52) U.S. Cl.
USPC ............................................................ 438/7

(58) Field of Classification Search
USPC ............................................................ 438/7
See application file for complete search history.

(56) References Cited

U.S. PATENT DOCUMENTS

| | | | |
|---|---|---|---|
| 6,603,538 B1 * | 8/2003 | Oluseyi et al. | 356/72 |
| 6,633,391 B1 | 10/2003 | Oluseyi et al. | |
| 6,762,849 B1 * | 7/2004 | Rulkens | 356/630 |
| 6,806,949 B2 * | 10/2004 | Ludviksson et al. | 356/72 |
| 6,894,769 B2 * | 5/2005 | Ludviksson et al. | 356/72 |
| 2002/0102858 A1 * | 8/2002 | Wicker et al. | 438/731 |
| 2003/0005943 A1 * | 1/2003 | Singh et al. | 134/1.1 |
| 2004/0040657 A1 * | 3/2004 | Ikuhara et al. | 156/345.24 |
| 2004/0069225 A1 * | 4/2004 | Fairbairn et al. | 118/715 |
| 2005/0070104 A1 * | 3/2005 | O'Meara et al. | 438/689 |

FOREIGN PATENT DOCUMENTS

| | | |
|---|---|---|
| JP | 04-186614 | 7/1992 |
| JP | 06-177073 | 6/1994 |
| JP | 09-162165 | 6/1997 |
| JP | 2002-057149 | 2/2002 |
| JP | 2002-324788 | 11/2002 |
| JP | 2003-077843 | 3/2003 |
| JP | 2003-209099 | 7/2003 |
| JP | 2003-229425 | 8/2003 |

OTHER PUBLICATIONS

Office Action issued Jul. 26, 2011, in Japanese Application No. 2006-533874 (English translation only).

* cited by examiner

*Primary Examiner* — William D Coleman
(74) *Attorney, Agent, or Firm* — Oblon, Spivak, McClelland, Maier & Neustadt, L.L.P.

(57) ABSTRACT

A method and system are provided for monitoring status of a system component in a process chamber of a batch type processing system. The method includes exposing a system component to light from a light source and monitoring interaction of the light with the system component to determine status of the system component. The method can detect light transmission and/or light reflection from a system component during a process that can include a chamber cleaning process, a chamber conditioning process, a substrate etching process, and a substrate film formation process. The system component can be a consumable system part such as a process tube, a shield, a ring, a baffle, and a liner, and can further contain a protective coating.

4 Claims, 11 Drawing Sheets

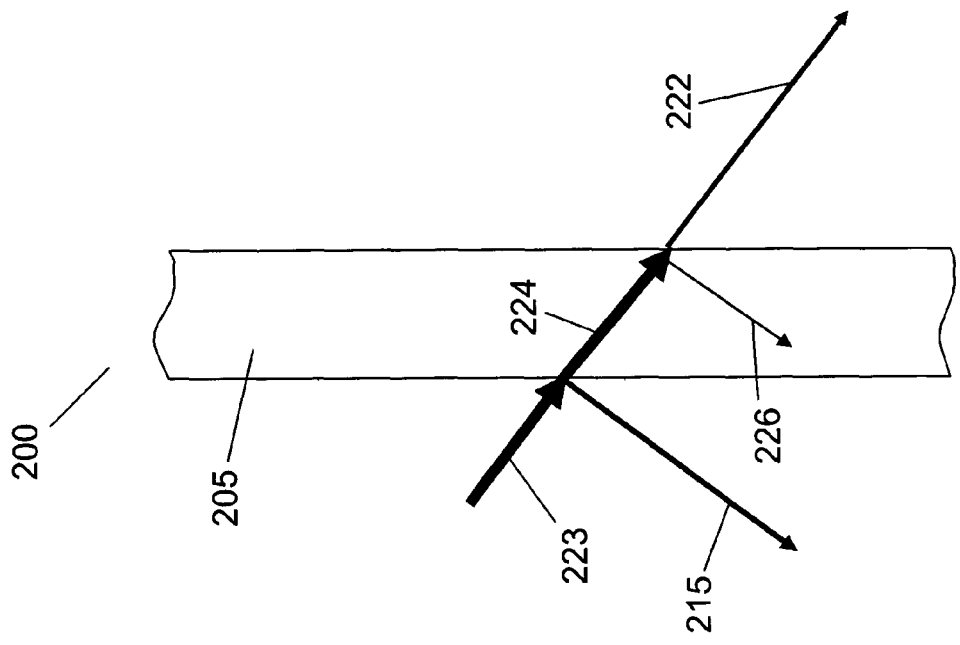
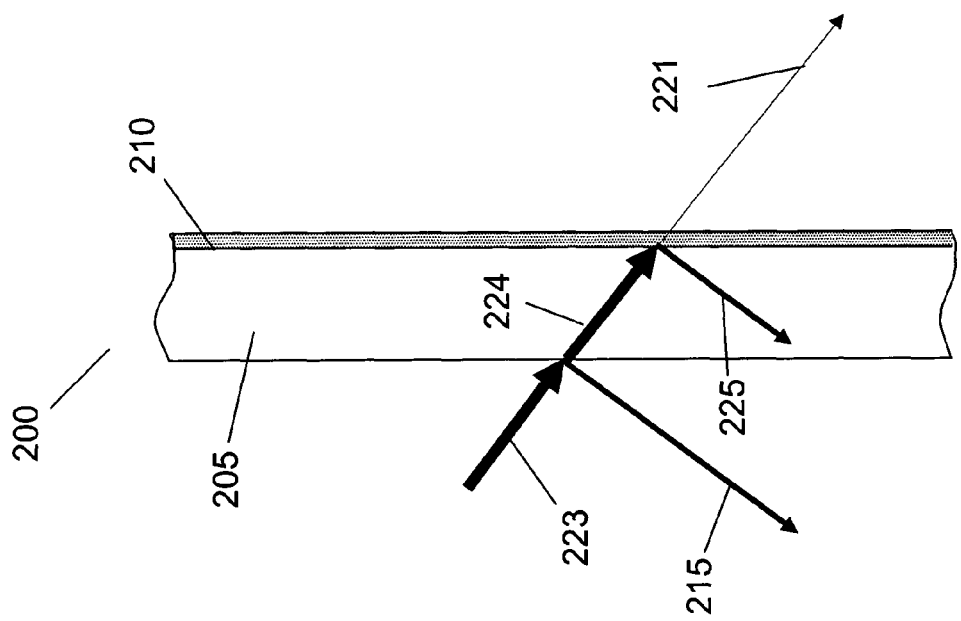

METHOD FOR MONITORING STATUS OF SYSTEM COMPONENTS

BACKGROUND OF THE INVENTION

1. Field of the Invention

The present invention relates to chamber processing, and more particularly to a method for monitoring the status of system components during a process performed in a batch type processing system.

2. Description of the Related Art

Many semiconductor fabrication processes are performed in process chambers such as for example plasma etch chambers, plasma deposition chambers, thermal processing chambers, chemical vapor deposition chambers, atomic layer deposition chambers, etc. Processing of substrates can lead to formation of material deposits on system components in the process chamber. Periodic dry cleaning of the process chambers can be carried out to remove the chamber deposits, where the cleaning process removes different material deposits from the system components.

Various parts of a processing system can include consumable or replaceable system components that can, for example, be fabricated from quartz, silicon, alumina, carbon, or silicon carbide. The consumable nature of the replaceable components requires frequent maintenance of the processing system. Consumable system parts are commonly replaced or cleaned after film accumulation threatens particle problems, for example between incompatible processes scheduled to be run in sequence, or after detrimental processing conditions, or when poor processing results are observed. Alternately, consumable system parts can be cleaned or replaced according to a predetermined maintenance schedule that can, for example, be based on the number of operating hours. Such maintenance approaches frequently result in overdue or premature replacement of the consumable system components.

Further complications arise because the length of a cleaning process, based on a fixed time period that has been proven to result in adequate cleaning of system components in the past, may differ depending on the history of the system components. Accordingly, the fixed time period may be unnecessarily long, may result in undesired etching (erosion) of the system components, and/or may not adequately restore the system component.

Chamber conditioning processes (also referred to as passivation processes) are commonly implemented in semiconductor fabrication to prepare process chambers for optimal performance. For example, chamber conditioning processes may be carried out following chamber cleaning, after an extended chamber idle period, or before a first chamber production process. When used with plasma chambers, chamber conditioning processes typically involve using a "conditioning plasma" in the plasma chamber for a predetermined length of time to prepare or "condition" the chamber for the upcoming performance of a plasma process involving production wafers. The parameters of the conditioning process (e.g., RF power, chamber and substrate temperature, feed gas composition, an pressure) are usually maintained at or near the parameters of the corresponding production process for which the chamber is being conditioned. In this manner, conditioning processes can help ensure that all processes performed in a process chamber produce results with in a desired range.

Conditioning processes can be performed on several wafers or sets of wafers. The extent of conditioning can be monitored by periodically analyzing the wafers during the conditioning procedure to determine process compliance. However, conditioning processes that are carried out for long time periods involve the use of a large number of test wafers, which result in large startup expenses. Alternatively, the extent of conditioning can be carried out for a fixed time period that has been proven to provide production process compliance. However, because the effectiveness of the conditioning process in not actually monitored, the fixed time period may be unnecessarily long in order to account for varying conditioning times required to achieve process compliance for different runs of a conditioning process. This can result in unacceptable reduction in throughput for the processing chamber.

SUMMARY OF THE INVENTION

Accordingly, one object of the present invention is to provide a mechanism for in-situ monitoring of a system component in a processing system.

Another object of the present invention is to provide a method and system for monitoring a status of a system component in a process chamber of a batch type processing system.

Various of these and/or other objects of the present invention are provided by a method for monitoring a status of a system component in a process chamber of a batch type processing system by exposing a system component to light from a light source and monitoring interaction of the light with the system component to determine the status of the system component.

In one aspect of the present invention, the method includes carrying out a process in the process chamber, where the process can include a chamber cleaning process, a chamber conditioning process, a substrate etching process, and a substrate deposition process.

In another aspect of the present invention, a processing system is provided for monitoring a status of a system component. The processing system includes a process chamber configured for performing a process, a light source to expose the system component to light, an optical monitoring system configured for monitoring interaction of the light with the system component to determine status of the system component, and a controller configured to control the processing system.

In another aspect of the present invention, the processing system includes a gas injection system configured for introducing a process gas in the process chamber to facilitate a process in the process chamber.

The system components monitored can include a consumable system part such as for example a process tube, a shield, a ring, a baffle, and a liner. Further, the system components monitored, including the consumer system parts, can have a protective coating.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2A is a schematic showing a cross-sectional view of interaction of light with a system component containing a material deposit in accordance with an embodiment of the invention;

FIG. 2B is a schematic showing a cross-sectional view of interaction of light with a clean system component according to an embodiment of the invention;

DETAILED DESCRIPTION OF THE PREFERRED EMBODIMENTS

As noted above, processes for cleaning and conditioning system components in a batch type processing system are typically not monitored for the status of the system components. Therefore, cleaning and conditioning processes can be overdue, premature, or be carried out for a time period that is too short or unnecessarily long. Nevertheless, in-situ monitoring of system component status has not been implemented, perhaps due to lack of effective methods for integrating in-situ monitoring of system components into processing systems and perhaps due to the perception that erosion of system components during regular chamber cleaning causes a significant change in the optical properties of the system component. However, the present invention realizes that in-situ exposure of a system component to light from a light source, and monitoring of interactions of the light with the system component can provide a feasible mechanism for monitoring status of a system component and can be effectively integrated in a process chamber of a batch type processing system.

Figure 1A:
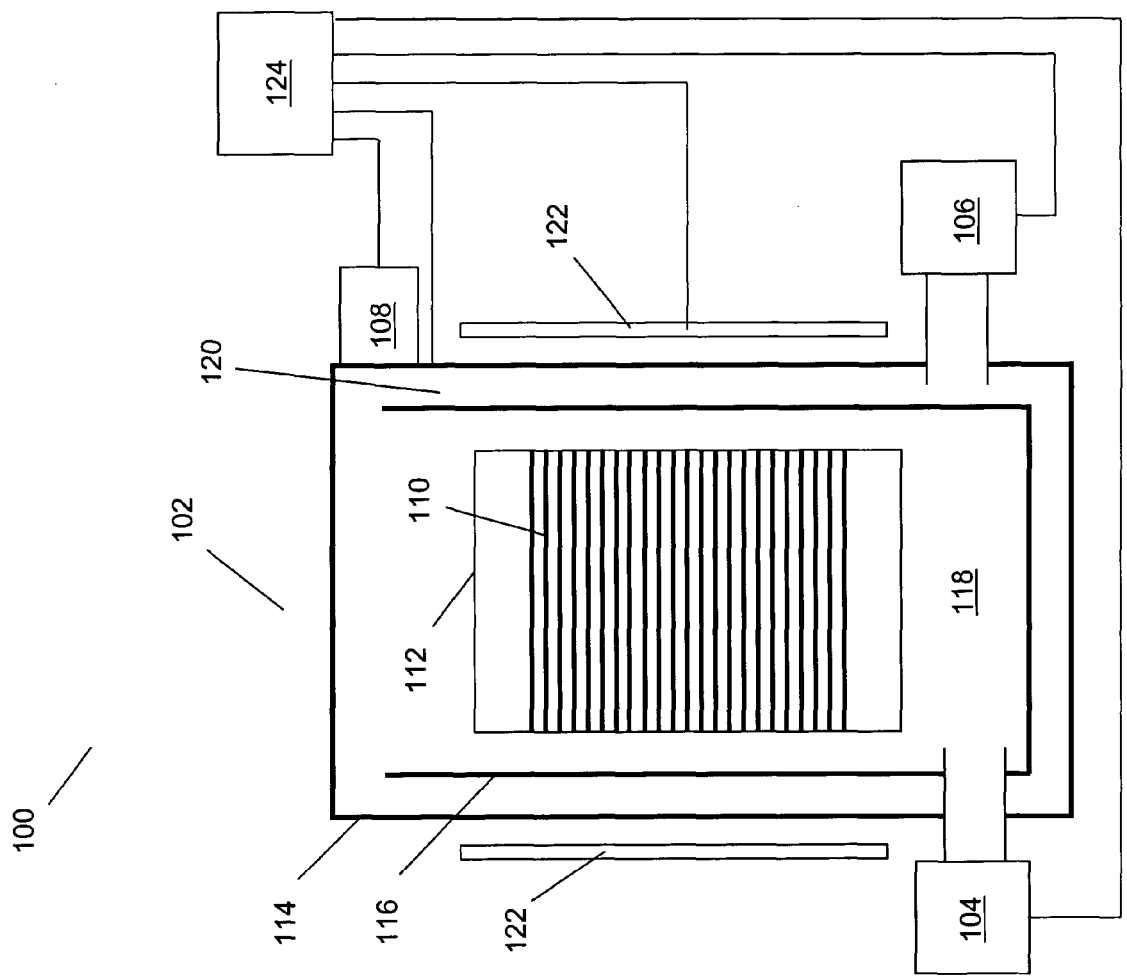
FIG. 1A is a simplified block diagram of a batch type processing system in accordance with one embodiment of the invention.

Referring now to the drawings, wherein like reference numerals designate identical, or corresponding parts throughout the several views, and more particularly to FIG. 1, FIG. 1A shows a simplified block diagram of a processing system according to an embodiment of the invention. The batch type processing system 100 can, for example, be a thermal processing system, a plasma processing system capable of sustaining a plasma, a chemical vapor deposition processing system, or an atomic layer deposition system. As illustrated in FIG. 1, the batch type processing system 100 includes a process chamber 102, a gas injection system 104, a heater 122, a vacuum pumping system 106, a chamber protection system 108, and a controller 124. Multiple substrates 110 can be loaded into the process chamber 102 and processed using substrate holder 112. Furthermore, the process chamber 102 has an outer section 114 and an inner section 116. In one embodiment of the present invention, the inner section 116 includes a process tube.

The gas injection system 104 introduces gases into the process chamber 102 for a number of purposes including but not limited to purging the process chamber 102, preparing the process chamber 102, cleaning the process chamber 102, and processing the substrates 110. A plurality of gas injector lines can be arranged to flow gases into the process chamber 102. The gases can be introduced into volume 118, defined by the inner section 116, and exposed to substrates 110. Thereafter, the gases can flow into the volume 120, defined by the inner section 114 and the outer section 116, and exhausted from the process chamber 102 by the vacuum pumping system 106.

Substrates 110 can be loaded into the process chamber 102 and processed using substrate holder 112. The batch type processing system 100 can allow for a large number of tightly stacked substrates 110 to be processed, thereby resulting in high substrate throughput. A substrate batch size can, for example, be about 100 substrates (wafers), or less. Alternately, the batch size can be about 25 substrates, or less. The processing system 100 can be configured to process substrates of various sizes, for example 200 mm substrates, 300 mm substrates, or larger substrates. The substrates 110 can, for example, include semiconductor substrates (e.g., Si or compound semiconductor), LCD substrates, and glass substrates.

The batch type processing system 100 can be controlled by a controller 124 capable of generating control voltages sufficient to communicate and activate inputs of the batch type processing system 100 as well as monitor outputs from the batch type processing system 100. Moreover, the controller 124 can be coupled to and exchange information with process chamber 102, gas injection system 104, heater 122, chamber protection system 108, and vacuum pumping system 106. For example, a program stored in the memory of the controller 124 can be utilized to control the aforementioned components of the batch type processing system 100 according to a desired process, and to perform any functions associated with monitoring the process. One example of controller 124 is a DELL PRECISION WORKSTATION 610™, available from Dell Corporation, Dallas, Tex.

Real-time process monitoring can be carried out using chamber protection system 108. The chamber protection system 108 can be positioned to monitor the gaseous environment in the process chamber 102. Alternately, the chamber protection system 108 can be positioned to monitor the process chamber effluent. In general, the chamber protection system 108 is a versatile monitoring system and can, for example, comprise a mass sensor (mass spectrometer) or an optical monitoring system (e.g., a Fourier Transform Infrared (FTIR) spectrometer) for monitoring light absorption by a process gas and reaction by-products. The chamber monitoring system 108, which is a process monitoring system, can provide qualitative and quantitative analysis of the gaseous environment in the process chamber 102. Process parameters that can be monitored using the chamber protection system 108 include process gas flows, gas pressure, ratios of gaseous species, gas purities, and reaction by-products including etch products.

A mass sensor is a readily available instrument for detection, identification, and monitoring of a gaseous environment in a processing system. A mass sensor can offer extreme sensitivity for detecting trace amounts of gaseous substances. Due to the relatively high pressure at the process monitoring point of a typical process, the gas sampling can include a pressure reduction system. The pressure reduction can be carried out using a length of capillary tube or a throttle valve, and the mass sensor itself can be pumped continuously. Infrared spectroscopy is a well-established analytical method for measuring light absorption of gases and is ideal for semiconductor process monitoring, because it can be used in both vacuum or non-vacuum environments and can provide a wealth of valuable information during a process.

Figure 1B:
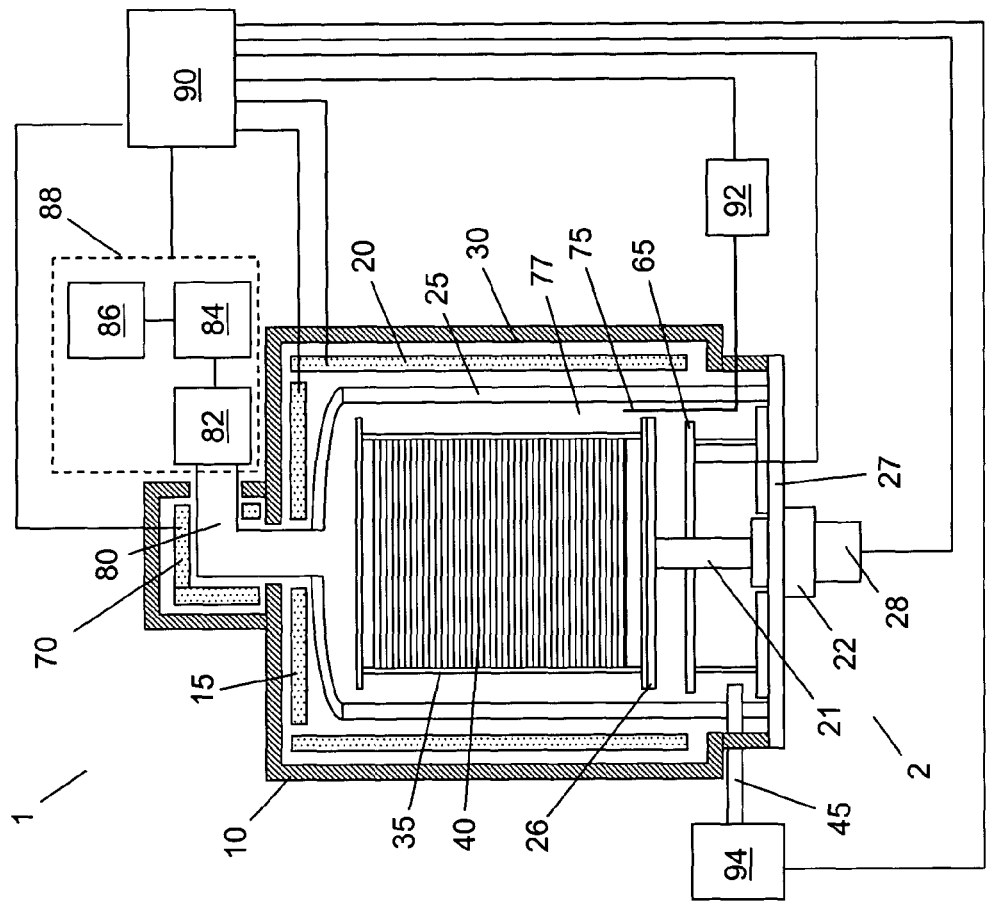
FIG. 1B is a simplified block diagram of another batch type processing system in accordance with one embodiment of the invention.

FIG. 1B shows a simplified block diagram of a processing system in accordance with another embodiment of the present invention. The batch type processing system 1 can, for example, be a thermal processing system or, alternately, the batch type processing system can be a plasma processing system capable of sustaining a plasma. The batch type processing system 1 contains a process chamber 10 and a process tube 25 that has an upper end connected to an exhaust pipe 80, and a lower end hermetically joined to a lid 27 of a cylindrical manifold 2, which includes those components of system 1 residing within the process tube 25 and removable therefrom, as well as the lid 27 and its operating components. The exhaust pipe 80 discharges gases from the process tube 25 to a vacuum pumping system 88 to maintain a predetermined atmospheric or below atmospheric pressure in the processing system 1. A substrate holder 35 for holding a plurality of substrates (wafers) 40 in a tier-like manner (in respective horizontal planes at vertical intervals) is placed in the processing zone 77 of the process tube 25. The substrate holder 35 resides on a turntable 26 that is mounted on a rotatable shaft 21 penetrating the lid 27 and driven by a motor 28. The turntable 26 can be rotated during processing to improve overall film uniformity or, alternately, the turntable 26 can be stationary during processing. The lid 27 is mounted on an elevator 22 for transferring the substrate holder 35 in and out of the reaction tube 25. When the lid 27 is positioned at its uppermost position, as shown in FIG. 1B, the lid 27 is adapted to close the open end of the manifold 2.

The processing system 1 can further include a pedestal (not shown) to provide thermal insulation between the substrate holder 35 and the manifold 2. In addition, the processing system 1, can include a cap cover (not shown) to protect the lid 27 from the processing environment. The pedestal and cap cover can, for example, be made of quartz or SiC.

A plurality of gas injector lines 45 can be arranged around the manifold 2 to supply a plurality of gases into the process tube 25 through the gas injector lines 45. In FIG. 1B, only one gas injector line 45 among the plurality of gas injector lines is shown. The gas injector line 45 is connected to a gas injection system 94. The process chamber 10 has a mirror-finished inner surface 30 to suppress dissipation of radiation heat radiated by main heater 20, bottom heater 65, top heater 15, and exhaust pipe heater 70. A helical cooling water passage (not shown) is formed within the wall of the process chamber 10 as a cooling medium passage.

A vacuum pumping system 88 typically includes a vacuum pump 86, a trap 84, and an automatic pressure controller (APC) 82. The vacuum pump 86 can, for example, include a dry vacuum pump capable of a pumping speed up to 20,000 liters per second (and greater). During processing, gases can be introduced into the process chamber 10 via the gas injection system 94 and the process pressure adjusted by the APC 82. The trap 84 can collect unreacted precursor material and by-products from the process chamber 10.

The chamber protection system 92 can be positioned to monitor the gaseous environment in the process chamber 10. Alternately, the chamber protection system 92 can be positioned to monitor the process chamber effluent. The chamber protection system 92 includes a sensor 75 capable of real-time process monitoring and can, for example, comprise a MS or a FTIR spectrometer. A controller 90 includes a microprocessor, a memory, and a digital I/O port capable of generating control voltages sufficient to communicate and activate inputs to the processing system 1 as well as monitor outputs from the processing system 1. Moreover, the controller 90 is coupled to and can exchange information with gas injection system 94, motor 28, chamber protection system 92, heaters 20, 15, 65, and 70, and vacuum pumping system 88.

It is to be understood that the processing systems in FIGS. 1A and 1B are for exemplary purposes only, as many variations of the specific hardware and software can be used to implement systems in which the present invention may be practiced, and these variations will be apparent to one having ordinary skill in the art. The processing systems in FIGS. 1A and 1B have system components that can erode, can become coated with material deposits, or can have a material deposit removed during processing. Consumable system components include process tubes, shields, rings, baffles, liners, and other system components found in batch type processing systems. In one embodiment of the present invention, the system components can be manufactured from a variety of materials that are transparent to light. The consumable system components can, for example, contain ceramic materials such as oxides, (e.g., quartz ($SiO_2$) and alumina ($Al_2O_3$)), nitrides (e.g., silicon nitride (SiN)), carbides (e.g., silicon carbide (SiC)). A system component can be constructed from a single type of material or, alternately, it can be constructed from more than one type of material.

Processing of substrates in a processing system can form a material deposit on the system component. A material deposit can contain one or more types of material, for example silicon (Si), silicon germanium (SiGe), silicon nitride (SiN), silicon dioxide ($SiO_2$), doped silicon, and dielectric materials including high-k metal oxides such as $HfO_2$, $HfSiO_x$, $ZrO_2$, $ZrSiO_x$. Monitoring etch products from the etching of many different material deposits can be unpractical due to a large number of etch products than can require monitoring.

In one embodiment of the present invention, a processing system can include a system component having a protective coating. A protective coating can, for example, protect a consumable system component from the processing environment during a process, and increase the lifetime of the consumable system component. A protective coating can be deposited on a system component in-situ, for example during a chamber conditioning process, or, alternately, a protective coating can be predeposited on the system component during manufacturing of the system component. A protective coating can, for example, include SiN, SiC, $SiO_2$, $Y_2O_3$, $Sc_2O_3$, $Sc_2F_3$, $YF_3$, $La_2O_3$, $CeO_2$, $Eu_2O_3$, $DyO_3$, $SiO_2$, MgO, $Al_2O_3$, ZnO, $SnO_2$, and $In_2O_3$.

In one embodiment of the present invention, a method is provided for monitoring a status of a system component in a process chamber of a batch type processing system by exposing a system component to light from a light source and monitoring interaction of the light with the system component to determine status of the system component. The monitoring can be carried out when a process is not being performed in the process chamber or, alternately, the monitoring can be carried out during a process. A process performed in the process chamber can, for example, include a substrate etching process, a substrate film formation process, a chamber cleaning process, and a chamber conditioning process.

The status of a system component can, for example, show a relative amount of a material deposit remaining on the system component during a chamber cleaning process where a material deposit is being removed from the system component, or a relative amount of a material deposit which may be formed on a system component during one or more of a substrate etching process, a substrate film formation process, or a chamber conditioning process.

A material deposit on the system component can contain one or more type of material, for example Si, SiGe, SiN, $SiO_2$, doped Si, and metal oxides such as $HfO_2$, $HfSiO_x$, $ZrO_2$, and $ZrSiO_x$. A material deposit can be removed in a cleaning process by exposing the system component to a process gas. The cleaning process can be stopped when the material deposit has been substantially removed from the deposited material before the system component material itself becomes eroded.

FIG. 2A schematically shows a cross-sectional view of the interaction of light with a system component containing a material deposit in accordance with an embodiment of the invention. The system component 200 can, for example, be a process tube, a shield, a ring, a baffle, or a liner. The system component 200 can be manufactured from a variety of materials, for example, quartz, SiC, and $Al_2O_3$. The system component 200 in FIG. 2A has a continuous smooth material deposit 210 formed onto the system component material 205. The material deposit 210 can contain one or more type of material, for example Si, SiGe, SiN, $SiO_2$, doped Si, and metal oxides such as $HfO_2$, $HfSiO_x$, $ZrO_2$, and $ZrSiO_x$.

In FIG. 2A, light 223 from a light source (not shown) is schematically shown interacting with the surface of system component material 205, resulting in reflected light 215 and transmitted light 224. Thereafter, transmitted light 224 is shown reflecting off the interface of the system component material 205 and material deposit 210 as light 225 and transmitted through the material deposit 210 as light 221. As may be appreciated by one skilled in the art, the abovementioned interaction of light 223 with the system component 200 can be a function of the wavelength of the light 223, the incident angle between the light 223 and the system component 200, and thickness, reflectivity, transmittance, and type of system component material 205 and the material deposit 210. Accordingly, in one embodiment of the present invention, a change in the intensity of transmitted light 221 and/or reflected light 225 can be used to monitor status of system component 200, including removal or buildup of material deposit 210 onto system component material 205.

In general, it is expected that signal intensity of transmitted light 221 will increase as a material deposit 210 is removed from system component 200 during a cleaning process and in some cases the signal intensity of reflected light 225 can decrease during a cleaning process. As mentioned above, the observed interaction of light 223 with system component 200 can depend on the material properties of the system component 200 and the choice of optical parameters (e.g., wavelength of light 223). A suitable setup that enables monitoring status of a system component 200 can be determined by direct experimentation and/or design of experiments (DOE).

FIG. 2B schematically shows a cross-sectional view of light interaction with a clean system component according to an embodiment of the invention. In FIG. 2B, material deposit 210 schematically shown in FIG. 2A has been removed in a process, resulting in a clean system component 200. The material deposit 210 can, for example, be removed in a cleaning process by exposing the system component 205 to a process gas. Removal of the material deposit 210 can result in transmitted light 222 that has a greater intensity than light 221 in FIG. 2A. Furthermore, the intensity of reflected light 226 in FIG. 2B can be less than the intensity of reflected light beam 225. In FIG. 2B, the material removal process has been stopped when the material deposit 210 has been removed from the system component material 205 and before the system component material 205 becomes eroded. By stopping the cleaning before significant erosion of the system component, the present invention can reduce the change in optical properties of the system component thereby facilitating future monitoring using the present invention.

While FIGS. 2A and 2B show optical monitoring by use of light incident on a surface of the system component opposite to the material deposit surface, the present invention is not limited to this configuration. In another embodiment of the present invention, incident light 223 can first be incident on and reflected from the material deposit 210 prior to reflecting from an interface between the material deposit 210 and the system component material 205 and prior to being transmitted through the system component material 205. The transmitted beam through the system component and/or the reflected beams can be used for monitoring of a status of the system component. Moreover, making the light incident on the material deposit side may allow monitoring the material deposit 210 by reflecting light only where a non-transparent system component is needed.

Figure 3:
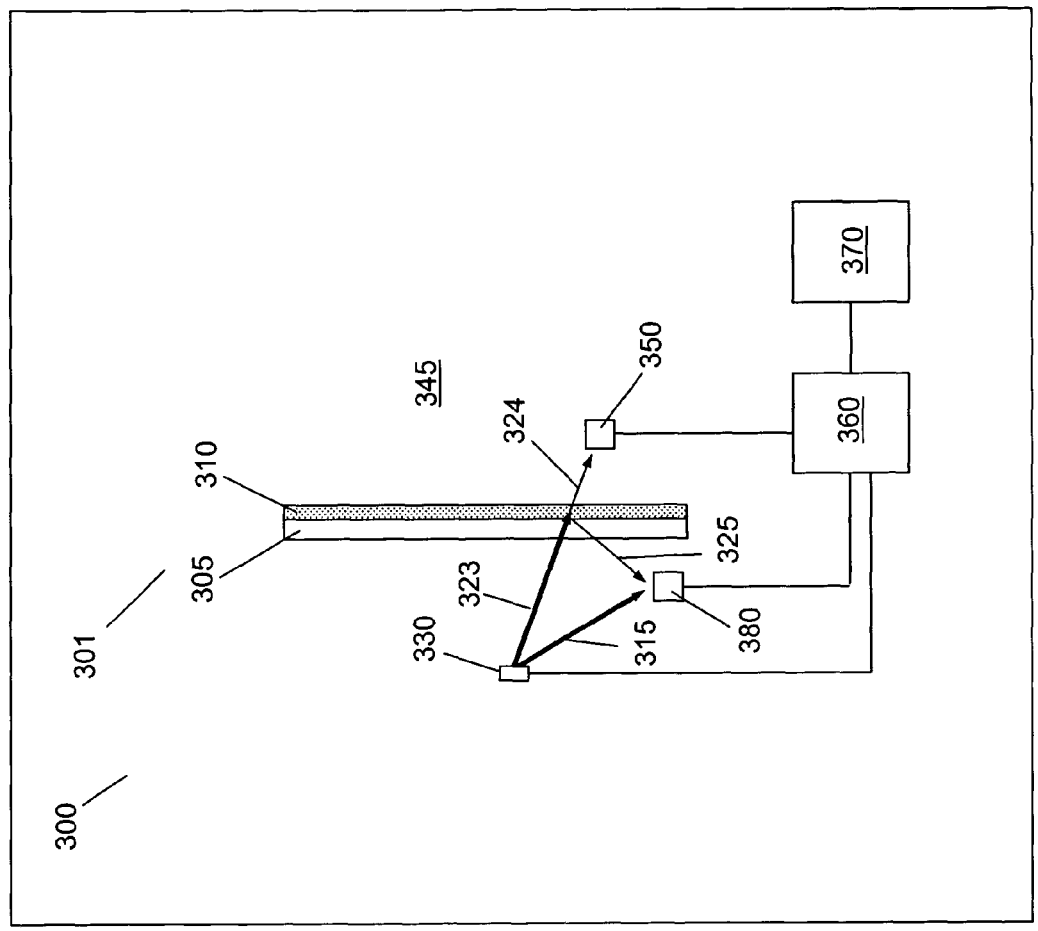
FIG. 3 is a schematic showing a cross-sectional view of a section of a processing system containing an optical monitoring system according to an embodiment of the invention.

FIG. 3 schematically shows a cross-sectional view of a section of a processing system containing an optical monitoring system according to an embodiment of the invention. The schematic shown in FIG. 3 is for exemplary purposes only, and can represent a section of the batch type processing systems in FIGS. 1A and 1B. The processing system 300 includes a system component 301 containing system component material 305 and material deposit 310, light source 330, light detectors 350 and 380, optical monitoring system 360, controller 370, and processing zone 345. The light detector 350 can be configured to detect transmitted light 324. The light detector 380 can be configured to detect reflected light 325 and reference light 315 from the light source 330. Light detectors 350 and 380, and the light source 330 can, for example, contain fiber optic components to transfer light signals to and from the optical monitoring system 360. The light source 330 can be positioned outside or inside the processing zone of the batch type processing system.

The light source 300 can, for example, be a laser. Alternately, the light source 300 can, for example, be a lamp or a light emitting diode (LED), that is capable of emitting light having wavelengths from ultra-violet to infrared. The light source 300 can emit light having a single wavelength or, alternately, light having multiple wavelengths. The light source 300 can, for example, include fiber optic components. In one example, the light source 300 can be a heater such as heater 20 in FIG. 1B. Such a heater may emit white light or may emit black body radiation thereby serving as a light source.

Deposition or removal of material deposits from light source 300 or light detectors 350 and 360 that are exposed to a process environment can affect the optical properties (e.g., light intensity from light source 300 or sensitivity of light detectors 350 and 360) of these optical components during processing. In order to maintain the optical properties of these optical components, they can, for example, be purged with an inert gas during processing. Those skilled in the art will readily appreciate that purge gas flow can be selected so as not to affect the process being performed in the process chamber, while at the same time being able to maintain the optical properties of the light source 300 and light detectors 350 and 360. Alternately, the abovementioned optical components can be heated to a temperature above the process temperature to reduce material deposition onto the optical components.

Figure 4:
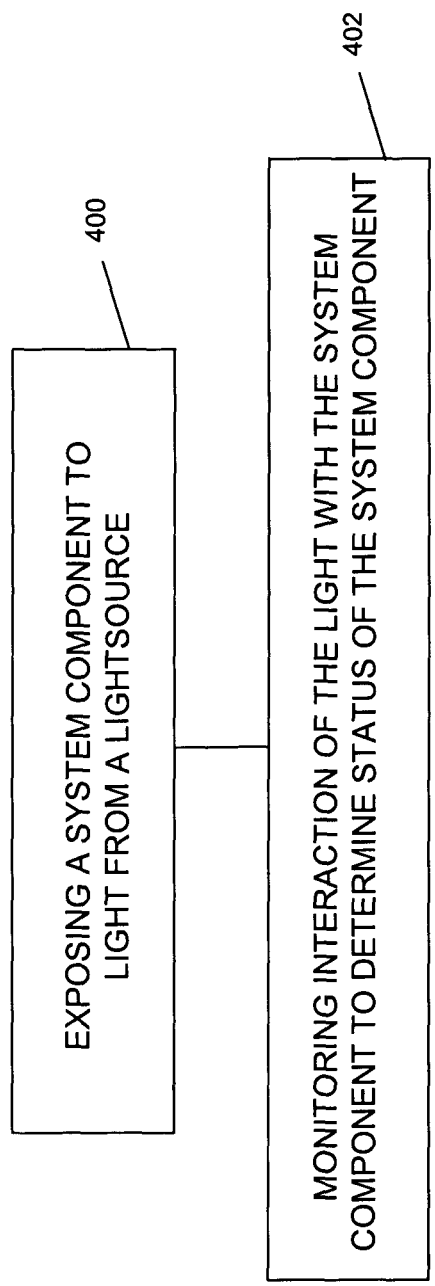
FIG. 4 is a flowchart showing a method of monitoring status of a system component in a batch type processing system in accordance with an embodiment of the invention.

FIG. 4 is a flowchart showing a method of monitoring status of a system component in a processing system according to an embodiment of the invention. In step 400, a system component is exposed to a light from a light source. In step 402, the interaction of the light with the system component is monitored to determine a status of the component. According to one embodiment of the invention, the interaction of light with a system component can monitored by detection and analysis of the transmitted or reflected light as schematically shown in FIG. 3.

In another embodiment of the present invention, the method, as illustrated in the flowchart in FIG. 4, can further include exposing the system component to a process, where the process may be a preparation or production process that is performed in a chamber and affects a status of a system component. For example, the process may utilize a process gas and be any type of deposition or etching process performed on a substrate in a chamber, or the process may be a chamber conditioning process or a chamber cleaning process used to prepare the chamber for semiconductor processing. During processing in the chamber, materials used for processing can be deposited or removed from the system component (and other surfaces inside the process chamber), altering transmitted or reflected light signals from interaction of light with the system component as the process continues in the process chamber. This change in the signal can be detected by the optical monitoring system and correlated to status of the system component.

In one embodiment of the present invention, a method is provided for monitoring status of a system component during a cleaning process. The cleaning process can include a process gas capable of removing a material deposit from a system component. In one embodiment of the present invention, a system component can contain quartz and the process gas can, for example, contain a cleaning gas including a halogen-containing gas (e.g., $ClF_3$, $F_2$, $NF_3$ and HF). The process gas can further contain an inert gas selected from at least one of Ar, He, Ne, Kr, Xe, and $N_2$.

Monitoring of a cleaning process can further include determining if an intensity level of transmitted or reflected light from a system component has reached a threshold value, arriving at a determination of whether the system component has been sufficiently cleaned, and based on the determination, either continuing with the cleaning process or stopping the cleaning process.

In one embodiment of the present invention, the chamber temperature can be between about 100° C. and about 1000° C. during a process. In another embodiment of the present invention, the chamber pressure can be between about 10 mTorr and about 760 Torr. In yet another embodiment of the present invention, the system components can made of quartz and a chamber cleaning process can include a chamber temperature of about 300° C. and a chamber pressure of about 200 mTorr.

In another embodiment of the present invention, a system component can have a protective coating and the process gas can be capable of removing a material deposit (such as for example a high-k metal oxide) from the system component. In one embodiment of the present invention, a system component can, for example, be manufactured from quartz and contain a SiN protective coating and a high-k material deposit.

In yet another embodiment of the present invention, a method is provided for monitoring status of a system component during a conditioning process, a substrate film formation process, or a substrate etch process by monitoring extent of material deposition onto the system component. The process gas can contain a chamber conditioning gas for conditioning a chamber, for example a silicon-containing gas such as dichlorosilane (DCS) and a nitrogen-containing gas such as $NH_3$, to form a silicon nitride coating on a system component to passivate and prevent contaminant outgassing; a film formation gas for forming a film on a substrate, for example a nitrogen-containing gas such NO or $N_2O$ for forming an oxide film or an oxynitride film on a substrate, a silicon-containing gas such as tetraethyl orthosilicate (TEOS) for depositing $SiO_2$ on substrate, or a metal-containing gas for forming a metal-oxide film (e.g., $HfO_2$) on a substrate; or a substrate etch gas for removing material from a substrate, for example a halogen-containing gas such HF for $SiO_2$ film removal. The process gas can further contain an inert gas selected from at least one of Ar, He, Ne, Kr, Xe, and $N_2$.

Monitoring of a chamber conditioning process, a substrate film formation process, or a substrate etching process can further include determining if an intensity level of transmitted light from a system component or reflected light from a system component has reached a threshold value, arriving at a determination of the extent of material deposition onto the system component, and based on the determination, either event, continuing with the process or stopping the process.

Figure 5:
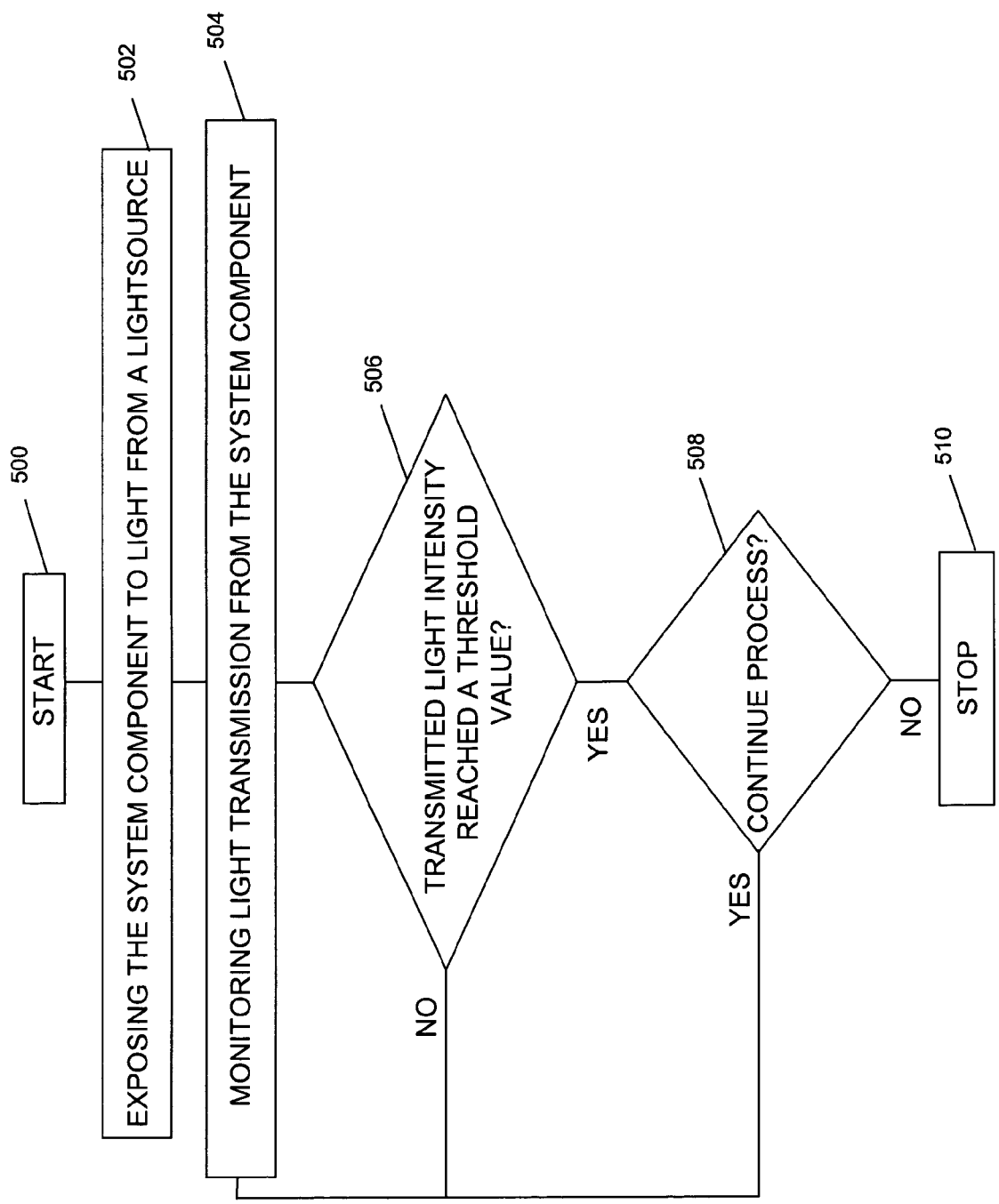
FIG. 5 is a flowchart showing a method of monitoring status of a system component in a batch type processing system in accordance with an embodiment of the invention.

FIG. 5 is a flowchart showing a method of monitoring status of a system component in a batch type processing system in accordance with an embodiment of the present invention. In step 500, the process is started. In step 502, a system component is exposed to a light from a light source, and in step 504, light transmission from the system component is monitored. In step 506, if the detected signal intensity of the transmitted light has not reached a threshold value, the process is continued in step 504, or if the signal in step 506 has reached a threshold value, a decision is made in step 508 whether to continue the process in step 504 or to stop the process in step 510.

Figure 6:
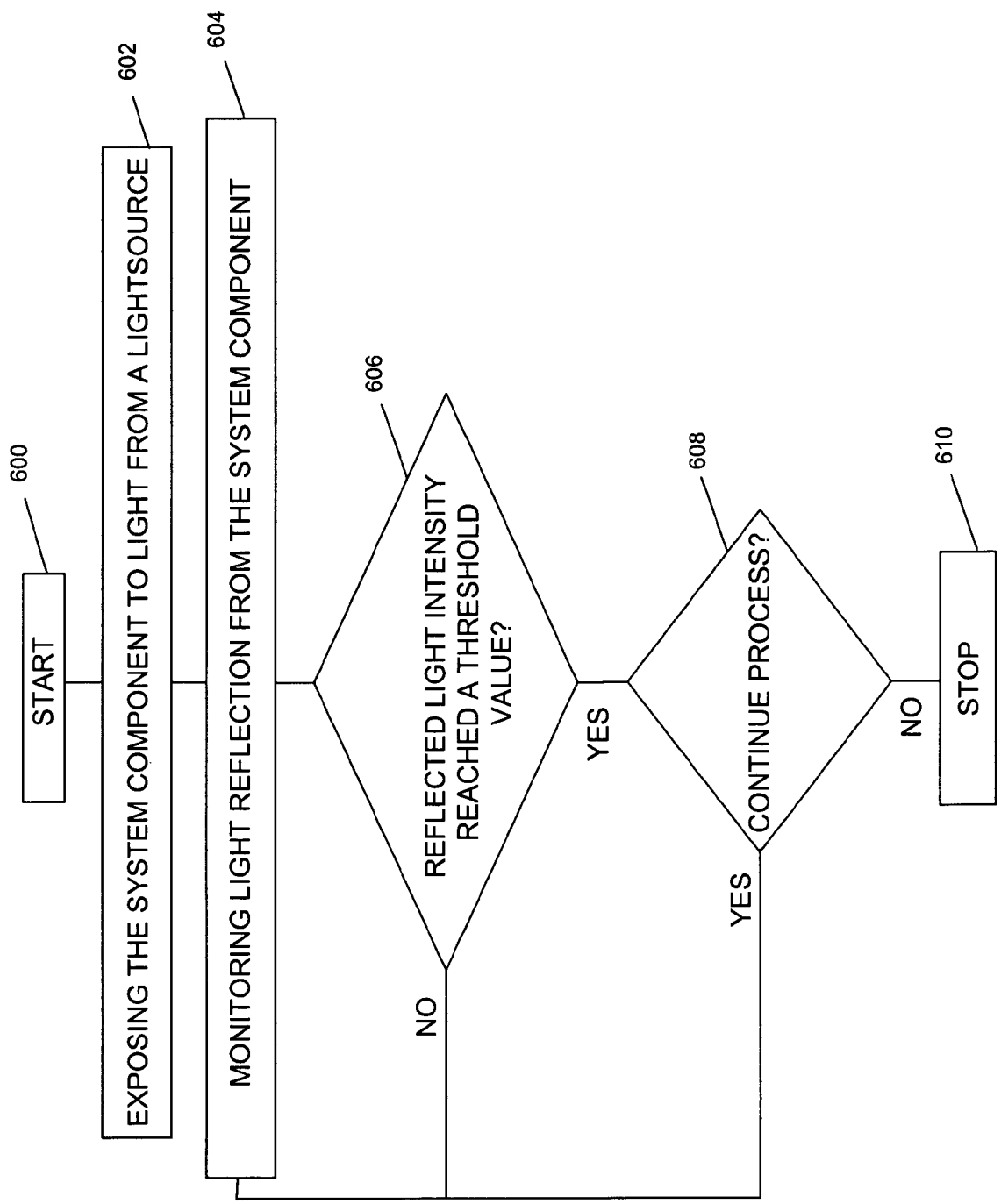
FIG. 6 is a flowchart showing a method of monitoring status of a system component in a batch type processing system in accordance with an embodiment of the invention.

FIG. 6 is a flowchart showing a method of monitoring status of a system component in a processing system in accordance with an embodiment of the present invention. In step 600, the process is started. In step 602, a system component is exposed to a light from a light source, and in step 604, light reflection from the system component is monitored. In step 604, if the detected signal intensity of the reflected light has not reached a threshold value, the process is continued in step 604, or if the signal in step 606 has reached a threshold value, a decision is made in step 608 whether to continue the process in step 604 or to stop the process in step 610.

In one example, signals of transmitted and reflected light from a system component can be combined to monitor status of a system component. In one example, a ratio of transmitted and reflected light intensities can be used to monitor status of a system component to provide improved detection sensitivity. In another example, a reference light from a light source can be compared to the transmitted and/or reflected light intensity.

Intensity of a light signal from the interaction of light with a system component be monitored to determine an endpoint of a process. Correlation of a signal intensity to an endpoint of a process can be carried out by test process that is performed while detecting a signal intensity and monitoring status of a system component. Status of a system component can, for example, be evaluated by inspecting the system component during the test process and correlating the inspected results to a detected threshold intensity recorded when a desired endpoint of the process is observed. The threshold intensity may be a fixed intensity value, a ratio of measured signal intensity and a reference signal intensity, or a ratio of measured signal intensity and initial signal intensity (measured at the start of the process).

Figure 7A:
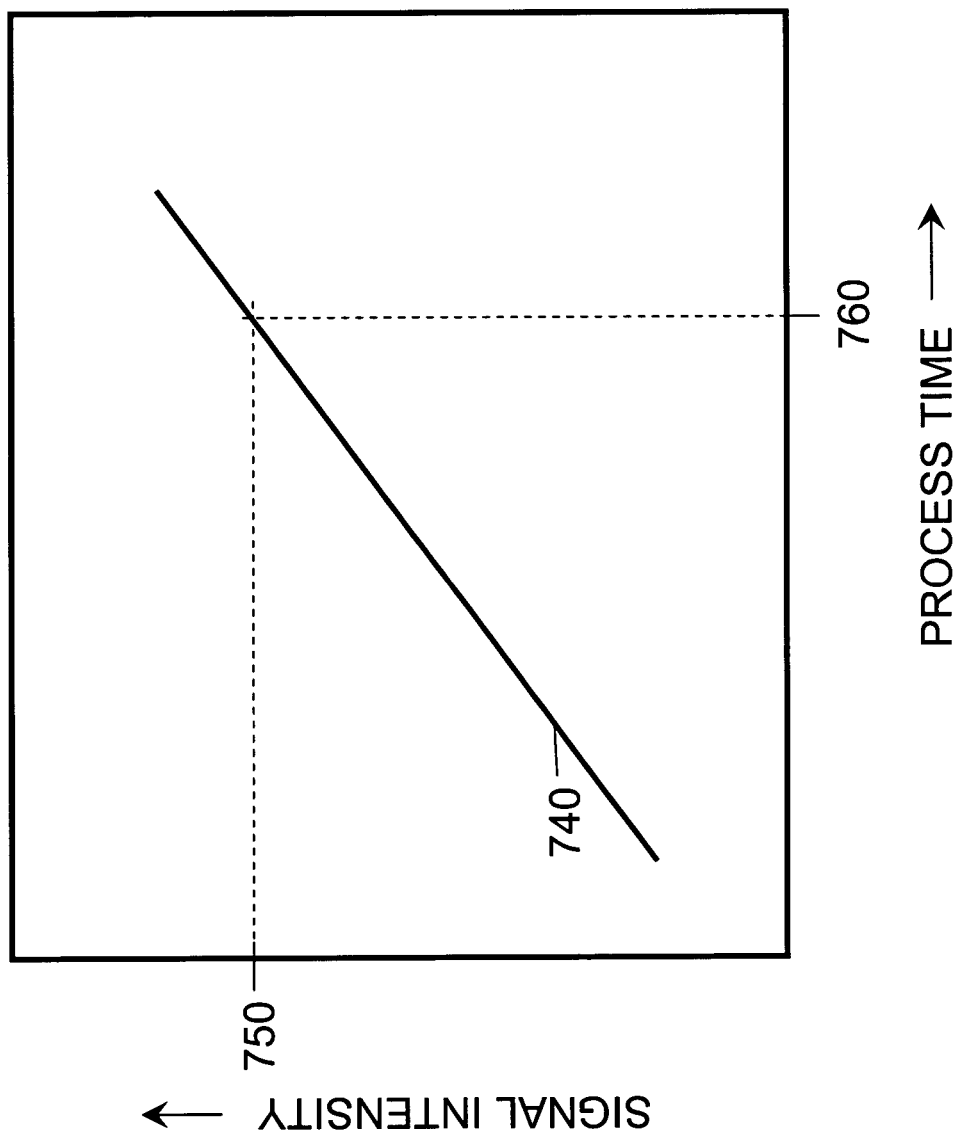
FIG. 7A is a graph showing light intensity as a function of process time for monitoring status of a system component in accordance with an embodiment of the invention.

FIG. 7A is a graph showing signal intensity as a function of processing time for monitoring a system component during a process in accordance with an embodiment of the invention. The system component can, for example, contain quartz. The curve 740 can, for example, be obtained by monitoring transmitted light (e.g., light 324 in FIG. 3) from a system component during a cleaning process where a material deposit is removed from the system component. Alternately, the curve 740 can be obtained by monitoring reflected light (e.g., light 325 in FIG. 3) from a system component during a process, where a material deposit is formed on the system component. The process can, for example, be a chamber conditioning process, a substrate film formation process, or a substrate etch process. As seen by the curve 740, the detected signal intensity generally increases as the process takes place. As seen in FIG. 7A, a threshold intensity 750 is detected at time 760. The threshold intensity 750 can, for example, indicate when the system component is known to be at an acceptable level for a desired process. The threshold intensity can, for example, indicate when the system component is known to be at an acceptable clean level for a cleaning process or at an acceptable conditioning level from a conditioning process. It is to be understood that an acceptable clean or conditioning level may vary depending on the production process to be performed in the chamber. While the curve 740 in FIG. 7A shows a substantial linear increase in signal intensity, it is to be understood that the signal intensity curve depends on the characteristics of the cleaning process and may be non-linear.

Figure 7B:
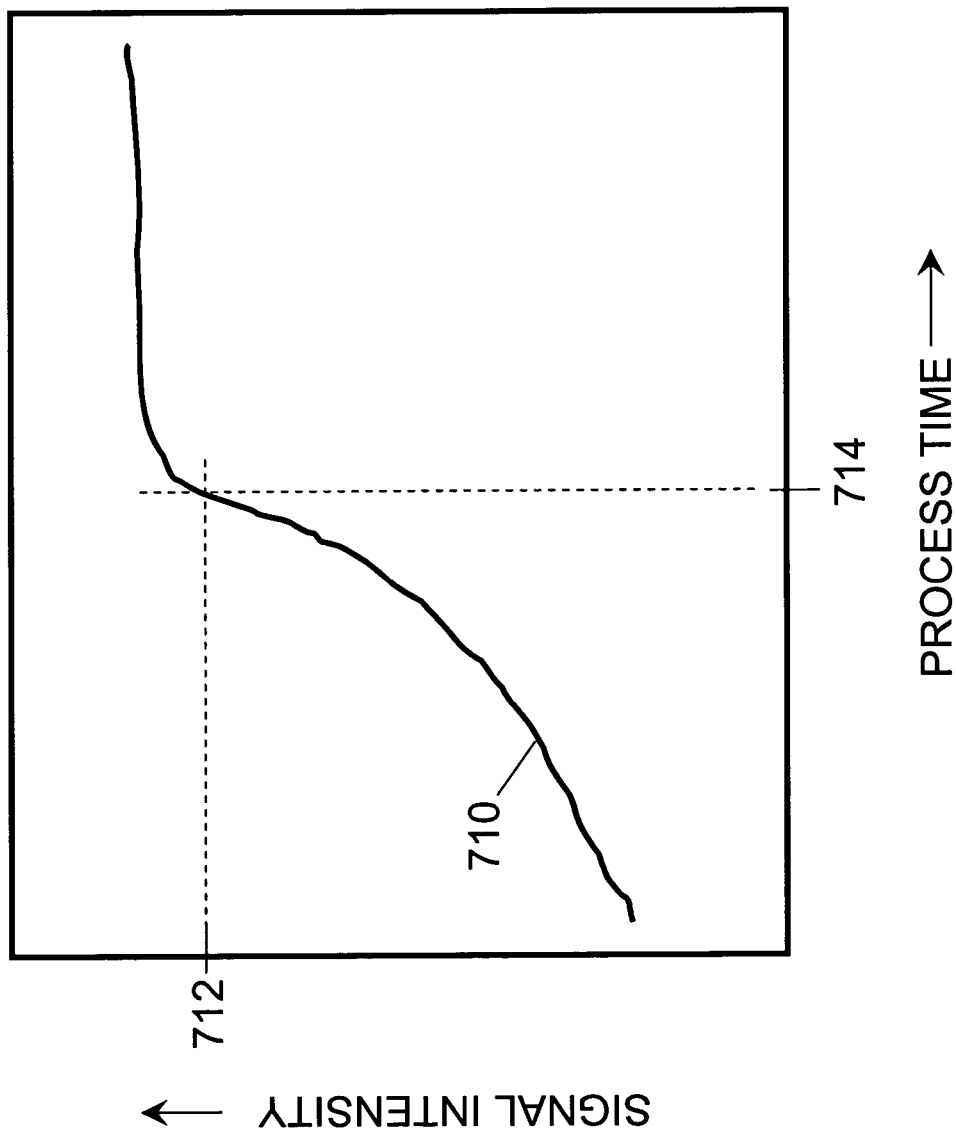
FIG. 7B is a graph showing light intensity as a function of process time for monitoring status of a system component in accordance with an embodiment of the invention.

FIG. 7B is a graph showing signal intensity as a function of processing time for monitoring a system component during a process according to an embodiment of the invention. In FIG. 7B, the signal intensity curve is non-linear where a threshold intensity 712 is detected at time 714 during a process, and at longer processing time, the signal in curve 710 becomes saturated. Threshold intensity 712 at time 714 can correspond to a signal intensity detected at a time when a desired status (e.g., clean level) of the system component has been achieved, for example, near complete removal of a material deposit from the system component in a cleaning process. If the cleaning process is capable of eroding the system component material and the process is carried out past time 714, erosion of the system component can occur.

Returning to FIGS. 5 and 6, as a signal intensity is detected in step 502 or step 602 during the process, a controller compares in step 504 or step 604 the detected signal intensity with prior stored signal intensity, or a reference signal intensity, and determines whether the detected signal intensity has reached the predetermined threshold intensity. When the signal threshold intensity is not yet detected in step 506 or step 606, the monitoring returns to step 504 or step 604, and the process continues. When the threshold signal intensity is detected in step 506 or step 606, a decision is made in step 508 or step 608 whether to continue the process in step 504 or step 604, or to stop the process in step 510 or step 610.

Figure 7C:
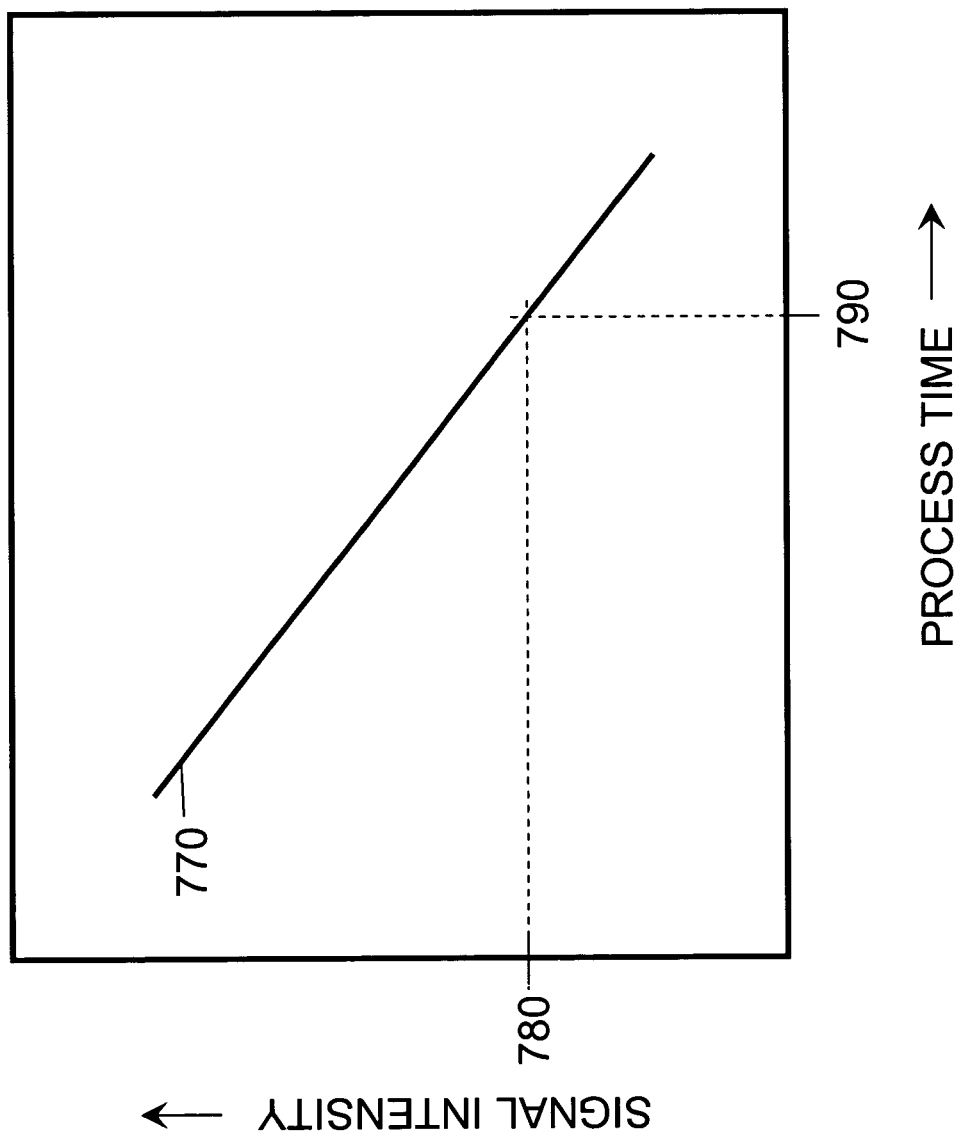
FIG. 7C is a graph showing light intensity as a function of process time for monitoring status of a system component in accordance with an embodiment of the invention.

FIG. 7C is a graph showing light intensity as a function of processing time for monitoring status of a system component in accordance with an embodiment of the invention. The curve 770 can, for example, be obtained by monitoring transmitted light from a system component during a process where a material deposit is formed on the system component, for example a chamber conditioning process, a substrate film formation process, or a substrate etch process. Alternately, the curve 770 can be obtained by monitoring reflected light from a system component during a cleaning process, where a material deposit is removed from the system component. As seen by the curve 770, the detected signal intensity generally decreases as the cleaning process takes place, and while the curve 770 in FIG. 7C shows a substantial linear decrease in signal intensity, it is to be understood that the signal intensity curve depends on the characteristics of the process and may be non-linear. As also seen in FIG. 7C, a threshold intensity 780 is detected at time 790. The threshold intensity can, for example, indicate when the system component is known to be at an acceptable clean level for a cleaning process or at an acceptable conditioning level for a conditioning process. It is to be understood that an acceptable clean or conditioning level may vary depending on the production process to be performed in the chamber.

Figure 8:
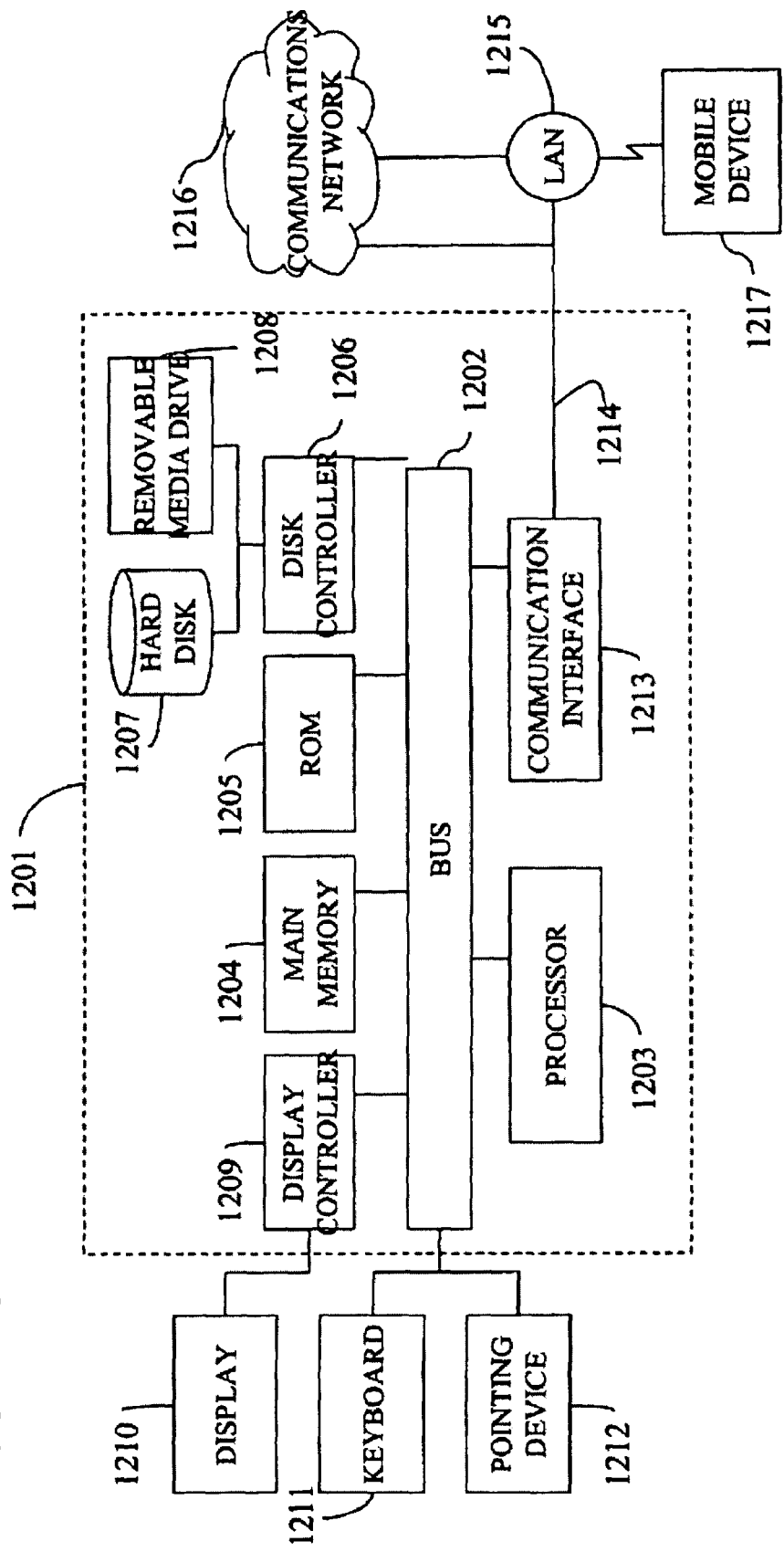
FIG. 8 is a depiction of a general purpose computer which may be used to implement the present invention.

As for the controllers of FIGS. 1A and 1B, the controller 370 may be implemented as a DELL PRECISION WORKSTATION 610™. Moreover, the controller of any of FIGS. 1A, 1B and 3 may be implemented as a general purpose computer system such as that described with respect to FIG. 8. FIG. 8 illustrates a computer system 1201 upon which an embodiment of the present invention may be implemented. The computer system 1201 may be used as the controller of FIGS. 1A, 1B, or 3, or a similar controller that may be used with the systems of these figures to perform any or all of the functions described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)). The computer system may also include one or more digital signal processors (DSPs) such as the TMS320 series of chips from Texas Instruments, the DSP56000, DSP56100, DSP56300, DSP56600, and DSP96000 series of chips from Motorola, the DSP1600 and DSP3200 series from Lucent Technologies or the ADSP2100 and ADSP21000 series from Analog Devices. Other processors especially designed to process analog signals that have been converted to the digital domain may also be used. The computer system may also include one or more digital signal processors (DSPs) such as the TMS320 series of chips from Texas Instruments, the DSP56000, DSP56100, DSP56300, DSP56600, and DSP96000 series of chips from Motorola, the DSP1600 and DSP3200 series from Lucent Technologies or the ADSP2100 and ADSP21000 series from Analog Devices. Other processors specially designed to process analog signals that have been converted to the digital domain may also be used.

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 maybe implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

Although only certain exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

The invention claimed is:

1. A method of monitoring status of a system component in a process chamber of a batch type processing system, comprising:
    exposing a system component of the batch type processing system to light from a light source; and
    monitoring interaction of the light with the system component to monitor a state of a material deposit on the system component in order to determine a status of the system component, and further comprising performing a process in the process chamber wherein the performing comprises:
    flowing a process gas including at least one of DCS and NH$_3$ during a chamber conditioning process.

2. A method of monitoring status of a system component in a process chamber of a batch type processing system, comprising:
    exposing a system component of the batch type processing system to light from a light source; and
    monitoring interaction of the light with the system component to monitor a state of a material deposit on the system component in order to determine a status of the system component, and further comprising performing a process in the process chamber, wherein the performing comprises:
    flowing a process gas including at least one of NO and TEOS during a substrate film formation process.

3. A method of monitoring status of a system component in a process chamber of a batch type processing system, comprising:
    exposing a system component of the batch type processing system to light from a light source; and
    monitoring interaction of the light with the system component to monitor a state of a material deposit on the system component in order to determine a status of the system component, and further comprising performing a process in the process chamber wherein the performing comprises:
    exposing a quartz system component to chamber pressure of about 200 mTorr and a temperature of about 300° C. during a chamber cleaning process.

4. A method of monitoring status of a system component in a process chamber of a batch type processing system, comprising:
    exposing a system component of the batch type processing system to light from a light source; and
    monitoring interaction of the light with the system component to monitor a state of a material deposit on the system component in order to determine a status of the system component, and further comprising performing a process in the process chamber wherein the exposing comprises:
    exposing a quartz system component including a SiN protective coating and a metal oxide material deposit to the light during a chamber cleaning process.

* * * * *